United States Patent [19]

Brissonnet et al.

[11] Patent Number: 5,607,680
[45] Date of Patent: Mar. 4, 1997

[54] MAKEUP REMOVER/SKIN CLEANSER COMPOSITIONS COMPRISING QUATERNARY PHOSPHATES AND PEG DIESTERS

[75] Inventors: Jean P. Brissonnet, Vouneuil sur Vienne; Véronique Burnier, Chatellerault, both of France

[73] Assignee: La Roche Posay Laboratoire Pharmaceutique, La Roche Posay, France

[21] Appl. No.: 429,637

[22] Filed: Apr. 27, 1995

[30] Foreign Application Priority Data

Apr. 27, 1994 [FR] France .................. 94 05087

[51] Int. Cl.⁶ .......................... A61K 7/48
[52] U.S. Cl. .................. 424/401; 514/844; 514/846; 514/937; 514/938; 514/944; 514/945
[58] Field of Search ............... 424/401; 514/937, 514/938, 944, 945, 844, 846

[56] References Cited

U.S. PATENT DOCUMENTS 5,135,748  8/1992  Ziegler et al. .................. 424/401

FOREIGN PATENT DOCUMENTS 0501714  9/1992  European Pat. Off. .
2055119  2/1981  United Kingdom .

*Primary Examiner*—Jyothsna Venkat
*Attorney, Agent, or Firm*—Burns, Doane, Swecker & Mathis, L.L.P.

[57] ABSTRACT

Cosmetic compositions well suited for removing makeup from the skin and/or eyes, and/or for the cleansing thereof, include a cosmetically acceptable vehicle or carrier comprising a fatty phase and an aqueous phase, and further comprise (a) a polyethylene glycol diester and (b) a quaternary phosphate of formula (I):

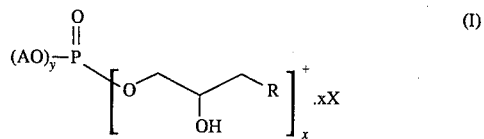

in which R is a cyclic, acyclic, aliphatic, aromatic or heterocyclic tertiary amine having at least 6 carbon atoms, X is an anion, A is an alkali metal, and x and y are two integers such that (x+y)=3, with the proviso that x cannot be zero.

21 Claims, No Drawings

MAKEUP REMOVER/SKIN CLEANSER COMPOSITIONS COMPRISING QUATERNARY PHOSPHATES AND PEG DIESTERS

BACKGROUND OF THE INVENTION

1. Technical Field of the Invention

The present invention relates to novel cosmetic compositions containing certain specific quaternary phosphate and diester compounds formulated into a vehicle comprising a fatty phase and an aqueous phase, and to the use of such novel compositions for removing makeup from the skin and/or eyes, or solely for cleansing the skin and/or eyes.

The present invention also relates to a technique for makeup removal which essentially consists of simply applying the composition to skin and/or eyes which have been made up.

2. Description of the Prior Art

The makeup removers traditionally used in this art are compositions having a high concentration of fatty substances whose function, when applied to the skin, is to dissolve and remove the various fats which are contained in makeup products, so as to remove them.

Thus, JP-A-55/150,402 describes the use of makeup removal compositions containing esters in which the total number of carbon atoms ranges from 17 to 36, with esters having from 23 and 28 carbon atoms being the preferred. The effective amount of these esters is at least 20% by weight relative to the total weight of the composition.

However, application of such makeup removal compositions having a high fat content creates annoyance or discomfort at the time of application, which manifests itself in a sensation of weight or heaviness on the face or of a veil over the eyes. Application of these compositions to the eyes can, moreover, cause a swelling of the eyelids.

The high fat concentration also presents the drawback of odor. It is consequently necessary to mask this odor via intense perfuming, and this can present other problems of tolerance.

In addition, as a result of their "heavy" texture, these makeup removers fail to impart a cool sensation, and they are difficult to apply and not easily rinsed off.

Indeed, after their application to the skin, such as that of the eyelids, rinsing with a tonic or water proves essential.

Thus, serious need continues to exist in this art for cosmetic compositions including a fatty phase and an aqueous phase, which does not require an obligatory rinse, which does not foam on application to the skin, and which contains only a minor fat concentration, while at the same time permitting proper makeup removal from the skin to be attained.

SUMMARY OF THE INVENTION

Accordingly, a major object of the present invention is the provision of improved makeup removal/skin cleansing compositions that avoid, or conspicuously ameliorate, the above disadvantages and drawbacks to date characterizing the state of this art.

Briefly, the present invention features novel cosmetic compositions comprising a fatty phase and including (a) at least one polyethylene glycol ("PEG") diester on the one hand and, on the other, (b) at least one specific quaternary phosphate compound having the following formula (I):

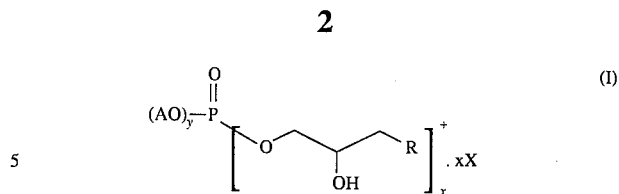

in which R is a tertiary amine having at least 6 carbon atoms and which can be cyclic or acyclic, aliphatic, aromatic or heterocyclic, X is an anion, A is an alkali metal, and E and X are two integers such that (x+y)=3, with the proviso that x cannot be zero.

DETAILED DESCRIPTION OF BEST MODE AND PREFERRED EMBODIMENTS OF THE INVENTION

More particularly, according to the present invention, the subject compositions permit the skin and/or the eyes to be cleansed, and/or makeup to be removed efficaciously therefrom, without any attendant irritation or any discomfort whatever to the user.

Moreover, the compositions of this invention present the advantage of effecting removal of makeup in the absence of an obligatory rinsing step; this is especially advantageous in the event of application to a skin having certain skin disorders or conditions, or in the case of application to the skin under conditions not conducive to rinsing with water, such as when travelling.

Another advantage presented by the compositions according to the invention is that they are well suited for the removal of any type of makeup product, including waterproof makeup products for the eyes or makeup products having fat-rich textures, such as foundations, powders and lipsticks that are particularly suited for making-up actors.

Lastly, another notable advantage presented by the compositions according to the invention is the fact that said compositions may be employed in hot countries where the use of excessively fat-rich makeup removers gives the sensation of weight or heaviness on the skin which is often difficult to bear.

According to this invention, the radical R is preferably an amidoamine structural unit having the following formula (II):

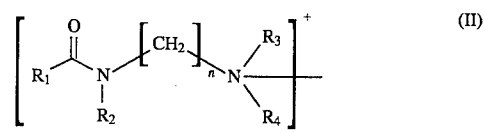

in which $R_1$ is an alkyl, alkenyl, alkoxy or hydroxyalkyl radical having from 5 to 22 carbon atoms, or an aryl or alkaryl radical having up to 20 carbon atoms; $R_2$ is a hydrogen atom, an alkyl, hydroxyalkyl or alkenyl radical having up to 6 carbon atoms, a cycloalkyl radical having up to 6 carbon atoms, and preferably from 2 to 5 carbon atoms, or a polyoxyalkylene radical having up to 10 carbon atoms; $R_3$ and $R_4$, which may be identical or different, are each an alkyl, hydroxyalkyl or carboxyalkyl radical having up to 6 carbon atoms in each alkyl moiety thereof, or a polyoxyalkylene radical having up to 10 carbon atoms, with the proviso that radicals $R_3$ and $R_4$ may together form, with the nitrogen atom from which they depend, a nitrogen-containing heterocycle; and n is an integer ranging from 2 to 10.

The anion comprising the quaternary phosphate compounds of formula (I) is preferably a halide, typically a fluoride, chloride or bromide ion.

The alkali metal employed is preferably selected from among sodium, lithium and potassium.

In a particularly preferred embodiment of the present invention, the compound of formula (I) is selected from among stearamidopropyl PG-dimonium chloride phosphate, linoleamidopropyl PG-dimonium chloride phosphate and cocamidopropyl PG-dimonium chloride phosphate.

This compound is advantageously formulated into the subject compositions in an amount ranging from 0.5% to 5% by weight, and preferably in an amount ranging from 1% to 2% by weight, relative to the total weight of the composition.

The diesters advantageously used for the preparation of the compositions according to the invention are those obtained by reacting a saturated or unsaturated fatty acid having from 16 to 22 carbon atoms with a polyethylene glycol in which the number of the oxyethylene recurring structural units ranges from 150 to 175.

Even more preferably, the diesters formulated into the subject compositions are selected from among polyethylene glycol distearates, polyethylene glycol dipalmitates, polyethylene glycol dioleates and polyethylene glycol dibehenates.

The diester comprising the subject compositions is advantageously present in an amount generally ranging from 1% to 5% by weight, and preferably in an amount ranging from 1% to 2% by weight, relative to the total weight of the composition.

The compositions according to the invention comprise, in addition, at least one fat constituting the fatty phase, and which is preferably selected from among fatty alcohols and oils having a melting point above 30° C.

Even more preferably, fatty alcohols are employed selected from among cetyl alcohol, stearyl alcohol and a mixture thereof. Among the oils having a melting point above 30° C., shea butter, illipe butter and cocoa butter are particularly representative.

In another especially preferred embodiment of the present invention, the aqueous phase comprising the compositions according to the invention represents at least 90% by weight, preferably at least 95% by weight and, even more preferably, at least 97% by weight of the total weight of the composition.

This aqueous phase of the compositions according to the invention preferably comprises water, in which at least one compound of the general formula (I) above is present.

The subject composition can optionally comprise, in addition, at least one perfume, and at least one preservative, in an amount ranging from 0.1% to 1% by weight relative to the total weight of the composition.

The compositions according to this invention may be formulated as an emulsion (water-in-oil, oil-in-water), a dispersion, a gel, a cream, a lotion or a foam, or any other form typically employed in the cosmetics art.

The present invention also features a technique for removing makeup from the skin, which comprises applying a composition as described above to skin and/or to eyes which have been made up. As indicated above, the application of this composition to the skin does not result in the generation of foam.

This technique optionally includes a rinsing step, which is not mandatory.

In order to further illustrate the present invention and the advantages thereof, the following specific example is given, it being understood that same is intended only as illustrative and in nowise limitative.

In said example to follow, all parts and percentages are given by weight, relative to the total weight of the composition.

EXAMPLE

A composition was formulated and used for removing makeup from the skin and/or cleansing the latter, in the form of a suspension.

The respective phases thereof were as follows:

Fatty phase:

Cetyl alcohol (consistency factor) 1
Stearyl alcohol (consistency factor) 1
Shea butter (emollient) 1.5
Polyethylene glycol distearate 2

Aqueous phase:

Cocamidopropyl PG-dimonium chloride phosphate 1
Preservative 0.1
Water qsp 100

This composition was prepared by introducing the fatty phase, at 75° C., into the aqueous phase, and then stirring the mixture to homogenize same. A perfume was lastly introduced in a sufficient amount, at a temperature below 50° C. after homogenization of the two phases.

This composition was used for cleansing the eyelids and the contours of the eyes, and also for the removal of makeup therefrom, both properly and without irritation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A makeup remover/skin cleanser cosmetic composition including a cosmetically acceptable vehicle comprising a fatty phase and an aqueous phase, and further comprising from 1% to 5% by weight of (a) a polyethylene glycol diester selected from the group consisting of polyethylene glycol distearate, polyethylene glycol dipalmitate, polyethylene glycol dioleate and polyethylene glycol dibehenate and from 0.5% to 5% by weight of (b) a quaternary phosphate of formula (I):

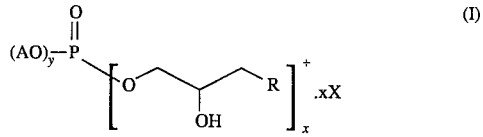

in which R is a cyclic, acyclic, aliphatic, or aromatic tertiary amine having at least 6 carbon atoms, X is an anion, A is an alkali metal, and x and y are two integers such that (x+y)=3, with the proviso that x cannot be zero.

2. The makeup remover/skin cleanser composition as defined by claim 1, wherein formula (I), R is an amidoamine structural unit of formula (II):

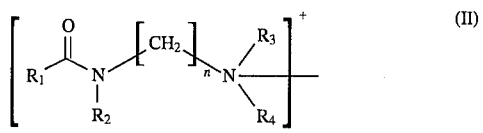

in which $R_1$ is an alkyl, alkenyl, alkoxy or hydroxyalkyl radical having from 5 to 22 carbon atoms, or an aryl or alkaryl radical having up to 20 carbon atoms; $R_2$ is a hydrogen atom, an alkyl, hydroxyalkyl or alkenyl radical having up to 6 carbon atoms, a cycloalkyl radical having up to 6 carbon atoms, or a polyoxyalkylene radical having up to 10 carbon atoms; $R_3$ and $R_4$, which may be identical or different, are each an alkyl, hydroxyalkyl or carboxyalkyl radical having up to 6 carbon atoms in each alkyl moiety thereof, or a polyoxyalkylene radical having up to 10 carbon atoms, and n is an integer ranging from 2 to 10.

3. The makeup remover/skin cleanser composition as defined by claim 1, wherein formula (I), X is a halide.

4. The makeup remover/skin cleanser composition as defined by claim 3, wherein formula (I), X is a chloride.

5. The makeup remover/skin cleanser composition as defined by claim 1, said compound of formula (I) comprising stearamidopropyl PG-dimonium chloride phosphate, linoleamidopropyl PG-dimonium chloride phosphate or cocamidopropyl PG-dimonium chloride phosphate.

6. The makeup remover/skin cleanser composition as defined by claim 1, said polyethylene glycol diester (a) comprising a diester of a fatty acid and polyethylene glycol, in which the fatty acid has from 16 to 22 carbon atoms and the polyethylene glycol backbone has from 150 to 175 ethylene oxide recurring structural units.

7. The makeup remover/skin cleanser composition as defined by claim 1, comprising at least one fatty alcohol or oil having a melting point above 30° C.

8. The makeup remover/skin cleanser composition as defined by claim 7, comprising cetyl alcohol, stearyl alcohol, isohexadecyl alcohol or mixture thereof.

9. The makeup remover/skin cleanser composition as defined by claim 7, comprising shea butter, illipe butter, cocoa butter or mixture thereof.

10. The makeup remover/skin cleanser composition as defined by claim 1, comprising from 1% to 2% by weight of said compound of formula (I) relative to the total weight of the composition.

11. The makeup remover/skin cleanser composition as defined by claim 1, comprising from 1% to 2% by weight of said polyethylene glycol diester (a) relative to the total weight of the composition.

12. The makeup remover/skin cleanser composition as defined by claim 1, said aqueous phase comprising at least 90% by weight thereof.

13. The makeup remover/skin cleanser composition as defined by claim 12, said aqueous phase comprising at least 95% by weight thereof.

14. The makeup remover/skin cleanser composition as defined by claim 13, said aqueous phase comprising at least 97% by weight thereof.

15. The makeup remover/skin cleanser composition as defined by claim 1, comprising an emulsion, gel, cream, lotion, or foam.

16. The makeup remover/skin cleanser composition as defined by claim 1, further comprising at least one perfume.

17. A method for the removal of makeup from skin and/or eyes to which makeup has been applied, comprising applying thereto an effective amount of the makeup remover/skin cleanser composition as defined by claim 1.

18. A method for cleansing skin and/or eyes in need of such treatment, comprising applying thereto an effective amount of the makeup remover/skin cleanser composition as defined by claim 1.

19. The method as defined by claim 17, further comprising rinsing the skin and/or eyes thus treated.

20. The method as defined by claim 18, further comprising rinsing the skin and/or eyes thus treated.

21. A composition of matter comprising from 1% to 5% by weight of (a) a polyethylene glycol diester selected from the group consisting of polyethylene glycol distearate, polyethylene glycol dipalmitate, polyethylene glycol dioleate and polyethylene glycol dibehenate and from 0.5% to 5% by weight of (b) a quaternary phosphate of formula (I):

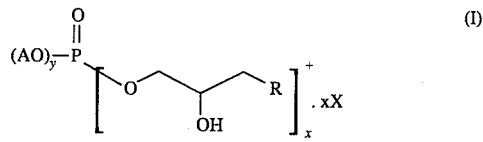

in which R is a cyclic, acyclic, aliphatic, or aromatic tertiary amine having at least 6 carbon atoms, X is an anion, A is an alkali metal, and x and y are two integers such that (x+y)=3, with the proviso that x cannot be zero.

* * * * *